US012557825B2

(12) United States Patent
Dekker

(10) Patent No.: US 12,557,825 B2
(45) Date of Patent: Feb. 24, 2026

(54) LACTOSE REDUCED DAIRY POWDER

(71) Applicant: DSM IP ASSETS B.V., Heerlen (NL)

(72) Inventor: Petrus Jacobus Theodorus Dekker, Echt (NL)

(73) Assignee: DSM IP ASSETS B.V., Heerlen (NL)

( * ) Notice: Subject to any disclaimer, the term of this patent is extended or adjusted under 35 U.S.C. 154(b) by 616 days.

(21) Appl. No.: 17/905,201

(22) PCT Filed: Mar. 9, 2021

(86) PCT No.: PCT/EP2021/055888
§ 371 (c)(1),
(2) Date: Oct. 27, 2022

(87) PCT Pub. No.: WO2021/180702
PCT Pub. Date: Sep. 16, 2021

(65) Prior Publication Data
US 2024/0180183 A1 Jun. 6, 2024

(30) Foreign Application Priority Data
Mar. 10, 2020 (EP) .................................... 20161956

(51) Int. Cl.
*A23C 9/12* (2006.01)
*A23C 9/16* (2006.01)
(Continued)

(52) U.S. Cl.
CPC .......... *A23C 9/1206* (2013.01); *A23C 9/1216* (2013.01); *A23C 9/16* (2013.01);
(Continued)

(58) Field of Classification Search
CPC ....... A23C 9/1206; A23C 9/1216; A23C 9/16; C12N 9/1051; C12N 9/2471; C12Y 204/01; C12Y 302/01023
(Continued)

(56) References Cited

U.S. PATENT DOCUMENTS

2012/0040051 A1 2/2012 Chen et al.

FOREIGN PATENT DOCUMENTS

CN 103547173 A 1/2014
CN 108138208 A 6/2018
(Continued)

OTHER PUBLICATIONS

International Search Report received in international application No. PCT/EP2021/055888, mailed May 17, 2021.
(Continued)

*Primary Examiner* — Brent T O'Hern
(74) *Attorney, Agent, or Firm* — McBee Moore & Vanik IP, LLC

(57) ABSTRACT

The present invention relates to the field of dry or powder dairy compositions. The invention provides a method for producing a lactose reduced dairy powder comprising treating a lactose comprising milk-based substrate with a first enzyme having transgalactosylase activity and a second enzyme having lactase activity to obtain a lactose reduced and galacto-oligosaccharides (GOS) comprising milk-based product; and preparing lactose reduced dairy powder from the lactose reduced and GOS comprising milk-based product.

21 Claims, 1 Drawing Sheet
Specification includes a Sequence Listing.

(51) Int. Cl.
    *C12N 9/10*         (2006.01)
    *C12N 9/38*         (2006.01)

(52) U.S. Cl.
    CPC ......... *C12N 9/1051* (2013.01); *C12N 9/2471*
        (2013.01); *C12Y 204/01* (2013.01); *C12Y*
        *302/01023* (2013.01)

(58) Field of Classification Search
    USPC ......................................................... 426/42
    See application file for complete search history.

(56)              References Cited

FOREIGN PATENT DOCUMENTS

| EP | 0 458 358 A1 | 11/1991 |
| EP | 3 228 194 A1 | 10/2017 |
| WO | 2012/160080 A1 | 11/2012 |
| WO | 2013/182686 A1 | 12/2013 |
| WO | 2015/086746 A1 | 6/2015 |
| WO | WO-2015095769 A1 * | 6/2015 | .......... A23C 9/1206 |
| WO | 2017120678 A1 | 7/2017 |
| WO | 2018/210821 A1 | 11/2018 |
| WO | 2020/117548 A1 | 6/2020 |

OTHER PUBLICATIONS

Torres et al., Technological Aspects of Lactose-hydrolyzed Milk Powder, Food Research International, 2017, vol. 101, pp. 45-53.

* cited by examiner

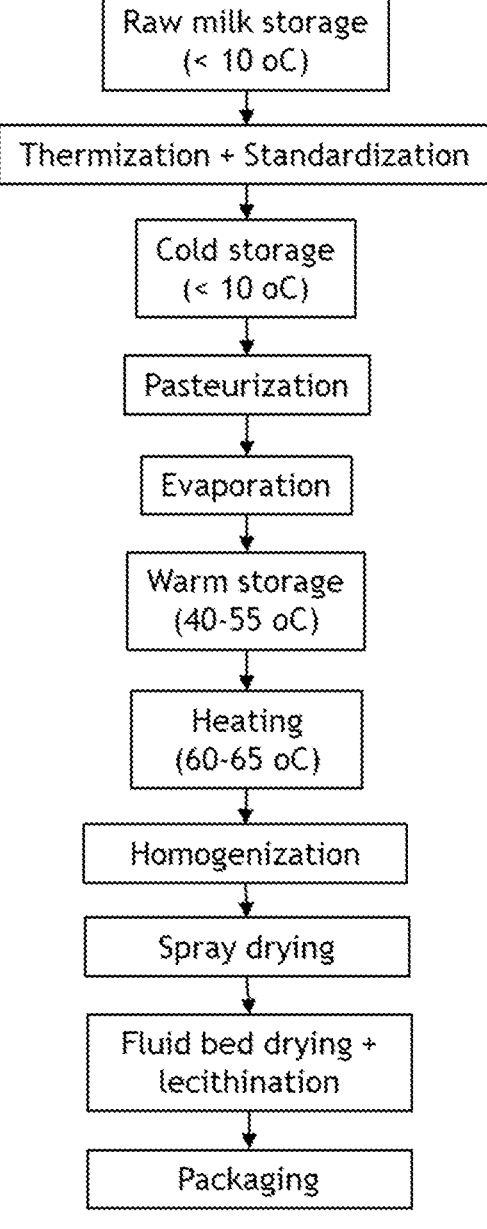

SEQUENCE LISTING

<160> NUMBER OF SEQ ID NOS: 7

<210> SEQ ID NO 1
<211> LENGTH: 594
<212> TYPE: PRT
<213> ORGANISM: Sporobolomyces singularis
<220> FEATURE:

<221> NAME/KEY: MISC_FEATURE
<222> LOCATION: (1)..(594)
<223> OTHER INFORMATION: Beta-hexosyltransferase of organism
      Sporobolomyces singularis (also referred to as BHT-132, wildtype)

<400> SEQUENCE: 1

```
Met Met Leu His Ala Ala Leu Leu Val Ala Leu Pro Cys Val Val Leu
1               5                   10                  15

Ala Arg Pro Ala Gly Ala Val Thr Tyr Pro Gly Ala Ile Pro Leu Ser
            20                  25                  30

Leu Thr Ser Asn Tyr Glu Thr Pro Ser Pro Thr Ala Ile Pro Leu Glu
            35                  40                  45

Pro Thr Pro Thr Ala Thr Gly Thr Ala Glu Leu Asp Ala Leu Trp Asn
    50                  55                  60

Leu Val Glu Ala Gln Tyr Pro Val Gln Thr Ala Ala Val Thr Thr Leu
65                  70                  75                  80

Val Thr Val Pro Asp Asp Tyr Lys Phe Glu Ala Asp Pro Pro Ser Tyr
                85                  90                  95

Ala Leu Ala Gly Tyr Glu Thr Ser Glu Ile Ala Gly Leu Lys Phe Pro
            100                 105                 110

Lys Gly Phe Lys Phe Gly Val Ala Gly Ala Ala Ile Gln Val Glu Gly
            115                 120                 125

Ala Ala Lys Ala Glu Gly Arg Gly Pro Ser Thr Trp Asp Tyr Leu Cys
    130                 135                 140

His His Tyr Ala Ser Thr Gln Cys Asn Asn Tyr Asp Pro Asp Ile Thr
145                 150                 155                 160

Thr Asn His Tyr Tyr Leu Tyr Pro Leu Asp Phe Ala Arg Leu Gln His
                165                 170                 175

Leu Gly Ile Asn Thr Tyr Ser Phe Ser Ile Ser Trp Thr Arg Ile Tyr
                180                 185                 190

Pro Leu Gly Ala Gly Tyr Val Asn Glu Ala Gly Leu Ala His Tyr Asp
            195                 200                 205

Ala Val Ile His Ser Ala Lys Lys Tyr Gly Leu Glu Pro Val Gly Thr
    210                 215                 220

Val Phe His Trp Asp Thr Pro Leu Ser Leu Met Leu Lys Tyr Gly Ala
225                 230                 235                 240

Trp Gln Asp Thr Gly Asp Gln Ile Val Lys Asp Phe Val Thr Tyr Ala
                245                 250                 255

Thr Thr Val Phe Lys Arg Tyr Gly Asn Glu Val Lys Thr Trp Phe Thr
                260                 265                 270

Phe Asn Glu Pro Arg Val Phe Cys Ser Gln Asn Ser Gly Leu Pro Tyr
            275                 280                 285

Asn Leu Thr Tyr Pro Glu Gly Ile Asn Ser Thr Ser Ala Val Phe Arg
    290                 295                 300

Cys Thr Tyr Asn Val Leu Lys Ala His Gly His Ala Val Lys Val Tyr
305                 310                 315                 320

Arg Asp Leu Val Ala Ser Gly Thr Ile Ala Ala Gly Glu Ile Gly Phe
                325                 330                 335

Lys Ser Asp Asp Asn Tyr Pro Ile Pro Ala Arg Pro Gly Asn Ala Asp
            340                 345                 350

Asp Glu Glu Ser Ala Lys Arg His Glu Ala Phe Arg Ile Gly Ile Phe
            355                 360                 365

Ala Gln Pro Val Tyr Gly Asn Gly Asp Tyr Pro Asp Val Val Lys Glu
    370                 375                 380
```

```
Thr Val Gly Asp Met Leu Pro Ala Leu Thr Asp Glu Asp Lys Gly Tyr
385             390             395             400

Ile Lys Gly Ser Gly Asp Ile Phe Ala Ile Asp Gly Tyr Arg Thr Asp
                405             410             415

Ile Ser His Ala Ala Leu Asn Gly Ile Ala Asn Cys Ile Arg Asn Gln
            420             425             430

Ser Asp Pro Asn Trp Pro Val Cys Glu Glu Gly Ser Asp Pro Phe Ala
            435             440             445

His Val Tyr Pro Ser Gly Phe Ala Ile Gly Gln Ser Ala Asp Pro Leu
            450             455             460

Ser Ser Trp Leu Val Asn Ser Ala Pro Phe Ile Arg Asp Gln Leu Lys
465             470             475             480

Phe Leu Thr Gln Thr Tyr Pro Ala Lys Gly Gly Ile Tyr Phe Ser Glu
                485             490             495

Phe Gly Trp Ala Glu Asp Ala Glu Tyr Asp Arg Gln Leu Leu Tyr Gln
                500             505             510

Ile Thr Trp Asp Gly Leu Arg Thr Gln Tyr Leu Thr Asp Tyr Leu Ser
                515             520             525

Gln Leu Leu Leu Ala Val His Lys Asp Gly Ile Asn Leu Arg Gly Ala
            530             535             540

Leu Thr Trp Ser Phe Val Asp Asn Trp Glu Trp Gly Leu Gly Met Gln
545             550             555             560

Gln Lys Phe Gly Phe Gln Phe Val Asn Gln Ser Asp Pro Asp Leu Thr
                565             570             575

Arg Thr Phe Lys Leu Ser Ala His Ala Tyr Ala Gln Phe Gly Arg Asn
                580             585             590

His Leu

<210> SEQ ID NO 2
<211> LENGTH: 557
<212> TYPE: PRT
<213> ORGANISM: Artificial Sequence
<220> FEATURE:
<223> OTHER INFORMATION: sets out the sequence of BHT-134 which is a
      deletion mutant derived from SEQ ID NO: 1 and the deletion starts
      at position 18 up to and including position 54

<400> SEQUENCE: 2

Met Met Leu His Ala Ala Leu Leu Val Ala Leu Pro Cys Val Val Leu
1               5               10              15

Ala Gly Thr Ala Glu Leu Asp Ala Leu Trp Asn Leu Val Glu Ala Gln
                20              25              30

Tyr Pro Val Gln Thr Ala Ala Val Thr Thr Leu Val Thr Val Pro Asp
            35              40              45

Asp Tyr Lys Phe Glu Ala Asp Pro Pro Ser Tyr Ala Leu Ala Gly Tyr
            50              55              60

Glu Thr Ser Glu Ile Ala Gly Leu Lys Phe Pro Lys Gly Phe Lys Phe
65              70              75              80

Gly Val Ala Gly Ala Ala Ile Gln Val Glu Gly Ala Ala Lys Ala Glu
                85              90              95

Gly Arg Gly Pro Ser Thr Trp Asp Tyr Leu Cys His His Tyr Ala Ser
                100             105             110

Thr Gln Cys Asn Asn Tyr Asp Pro Asp Ile Thr Thr Asn His Tyr Tyr
            115             120             125

Leu Tyr Pro Leu Asp Phe Ala Arg Leu Gln His Leu Gly Ile Asn Thr
            130             135             140
```

-continued

```
Tyr Ser Phe Ser Ile Ser Trp Thr Arg Ile Tyr Pro Leu Gly Ala Gly
145                 150                 155                 160

Tyr Val Asn Glu Ala Gly Leu Ala His Tyr Asp Ala Val Ile His Ser
                165                 170                 175

Ala Lys Lys Tyr Gly Leu Glu Pro Val Gly Thr Val Phe His Trp Asp
            180                 185                 190

Thr Pro Leu Ser Leu Met Leu Lys Tyr Gly Ala Trp Gln Asp Thr Gly
            195                 200                 205

Asp Gln Ile Val Lys Asp Phe Val Thr Tyr Ala Thr Thr Val Phe Lys
        210                 215                 220

Arg Tyr Gly Asn Glu Val Lys Thr Trp Phe Thr Phe Asn Glu Pro Arg
225                 230                 235                 240

Val Phe Cys Ser Gln Asn Ser Gly Leu Pro Tyr Asn Leu Thr Tyr Pro
                245                 250                 255

Glu Gly Ile Asn Ser Thr Ser Ala Val Phe Arg Cys Thr Tyr Asn Val
                260                 265                 270

Leu Lys Ala His Gly His Ala Val Lys Val Tyr Arg Asp Leu Val Ala
            275                 280                 285

Ser Gly Thr Ile Ala Ala Gly Glu Ile Gly Phe Lys Ser Asp Asp Asn
            290                 295                 300

Tyr Pro Ile Pro Ala Arg Pro Gly Asn Ala Asp Asp Glu Glu Ser Ala
305                 310                 315                 320

Lys Arg His Glu Ala Phe Arg Ile Gly Ile Phe Ala Gln Pro Val Tyr
                325                 330                 335

Gly Asn Gly Asp Tyr Pro Asp Val Val Lys Glu Thr Val Gly Asp Met
            340                 345                 350

Leu Pro Ala Leu Thr Asp Glu Asp Lys Gly Tyr Ile Lys Gly Ser Gly
            355                 360                 365

Asp Ile Phe Ala Ile Asp Gly Tyr Arg Thr Asp Ile Ser His Ala Ala
        370                 375                 380

Leu Asn Gly Ile Ala Asn Cys Ile Arg Asn Gln Ser Asp Pro Asn Trp
385                 390                 395                 400

Pro Val Cys Glu Glu Gly Ser Asp Pro Phe Ala His Val Tyr Pro Ser
                405                 410                 415

Gly Phe Ala Ile Gly Gln Ser Ala Asp Pro Leu Ser Ser Trp Leu Val
            420                 425                 430

Asn Ser Ala Pro Phe Ile Arg Asp Gln Leu Lys Phe Leu Thr Gln Thr
            435                 440                 445

Tyr Pro Ala Lys Gly Gly Ile Tyr Phe Ser Glu Phe Gly Trp Ala Glu
        450                 455                 460

Asp Ala Glu Tyr Asp Arg Gln Leu Leu Tyr Gln Ile Thr Trp Asp Gly
465                 470                 475                 480

Leu Arg Thr Gln Tyr Leu Thr Asp Tyr Leu Ser Gln Leu Leu Leu Ala
            485                 490                 495

Val His Lys Asp Gly Ile Asn Leu Arg Gly Ala Leu Thr Trp Ser Phe
            500                 505                 510

Val Asp Asn Trp Glu Trp Gly Leu Gly Met Gln Gln Lys Phe Gly Phe
            515                 520                 525

Gln Phe Val Asn Gln Ser Asp Pro Asp Leu Thr Arg Thr Phe Lys Leu
        530                 535                 540

Ser Ala His Ala Tyr Ala Gln Phe Gly Arg Asn His Leu
545                 550                 555
```

```
<210> SEQ ID NO 3
<211> LENGTH: 1782
<212> TYPE: DNA
<213> ORGANISM: Artificial Sequence
<220> FEATURE:
<223> OTHER INFORMATION: sets out a codon-adapted DNA sequence for
      expression of SEQ ID NO: 1 in Aspergillus niger

<400> SEQUENCE: 3
atgatgcttc acgctgctct ccttgttgct cttccttgcg ttgtccttgc tcgtcccgcc      60
ggtgctgtca cctaccccgg tgccatcccc ctctccctca cctcgaacta cgagactccc     120
agccctactg ccattcctct ggagcccacc cccactgcca ctggtactgc tgagctcgat     180
gccctctgga acttggttga ggctcagtac cccgtgcaga ctgctgccgt caccaccctc     240
gtcaccgttc ccgatgacta caagttcgag gccgatcctc ctagctacgc tcttgctgga     300
tacgagactt ctgagattgc tggtctgaag ttccccaagg cttcaagtt cggtgttgct      360 ggtgccgcca tccaggttga gggtgctgcc aaggccgagg gccgtggtcc ctccacctgg     420
gactacctct gccaccacta cgcctccacc cagtgcaaca actacgaccc tgacatcacc     480
accaaccact actacctcta ccccctcgac ttcgctcgtc tgcagcacct gggtatcaac     540
acctactctt tctccatctc ctggactcgc atctaccctc ttggtgctgg ctacgtcaac     600
gaggctggtc tggctcacta cgatgccgtc atccactctg ccaagaagta cggcttggag     660
cctgttggta ccgtcttcca ctgggatact cctctgagct tgatgctcaa gtacggtgcc     720
tggcaggaca ccggtgacca gattgtcaag gacttcgtca cctacgccac cactgtcttc     780
aagcgctacg gcaacgaggt caagacctgg ttcaccttca cgagcctcg tgtcttctgc      840 tctcagaact ccggtctgcc ctacaacctg acctacccag aaggcatcaa ctccacctcg     900
gcggtgttcc gctgcaccta caacgtcctc aaggcccacg ccacgccgt caaggtctac      960 cgtgatcttg ttgcctccgg taccattgct gctggtgaga tcggtttcaa gtccgacgac    1020
aactacccca tccccgctcg ccccggcaac gccgatgatg aggagtccgc caagcgtcac    1080
gaagcgttcc gtatcggtat cttcgctcag cccgtgtatg caacggtga ctaccccgat     1140 gtcgtcaagg agactgttgg tgacatgctt cccgccctca ccgacgagga caagggctac    1200
atcaagggct ccggtgacat cttcgccatt gacggctacc gcactgatat atctcacgct    1260
gccctcaacg gcattgccaa ctgcattcgc aaccagtccg accccaactg gcccgtctgc    1320
gaagaaggaa gcgacccctt cgctcacgtc taccctccg gattcgccat cggtcagtct     1380
gccgaccctc tgagcagctg gctggtcaac tctgctccct catccgtga ccagctcaag     1440 ttcctgaccc agacctaccc tgccaagggt ggtatctact ctccgagtt cggctgggcg     1500 gaagatgcgg aatacgaccg tcagctcctc taccagatca cctgggatgg cctgcgcacc    1560
cagtacctga ccgactacct cagccagctc ctccttgccg ttcacaagga tggcatcaac    1620
ctgcgtggag cgttgacctg gtcgttcgtc gacaactggg aatggggctt gggaatgcag    1680
cagaagttcg gtttccagtt cgtcaaccag tcggaccccg atctgacccg caccttcaag    1740
ctctccgccc acgcctacgc tcagttcggc cgcaaccacc tg                       1782
```

```
<210> SEQ ID NO 4
<211> LENGTH: 1671
<212> TYPE: DNA
<213> ORGANISM: Artificial Sequence
<220> FEATURE:
<223> OTHER INFORMATION: sets out a codon-adapted DNA sequence for
      expression of SEQ ID NO: 2 in Aspergillus niger
```

```
<400> SEQUENCE: 4
atgatgctcc acgctgcctt gcttgttgct ctcccctgcg ttgttctcgc cggtactgct       60
gagctcgatg ccctctggaa cctggttgaa gcgcagtacc ccgtgcagac tgctgctgtc      120
accactctcg tcaccgtccc cgatgactac aagttcgagg ccgaccctcc tagctacgcc      180
cttgctggct acgagacttc tgagatcgct ggtctgaagt tccccaaggg tttcaagttc      240
ggtgttgctg gtgctgctat ccaggttgag ggtgctgcca aggccgaggg ccgtggtccc      300
agcacctggg actacctctg ccaccactac gccagcaccc agtgcaacaa ctacgacccc      360
gatatcacca ccaaccacta ctacctgtac cctctcgact cgctcgctt acaacacctg       420 ggcatcaaca cctactcttt ctccatcagc tggactcgta tctacccccct tggtgctgga     480 tacgtcaacg aggctggtct tgctcactac gatgccgtca tccactccgc caagaagtac      540
ggcttggagc ctgttggtac cgtcttccac tgggatactc ctctttctct gatgctcaag      600
tacggtgcct ggcaggacac tggtgaccag attgtgaagg acttcgtcac ctacgccacc      660
accgtcttca agcgttacgg caacgaggtc aagacctggt tcaccttcaa cgagcctcgt      720
gtcttctgct cgcagaactc cggtctgccc tacaacttga cttaccccga gggtatcaac      780
tccacctccg ccgtcttccg ctgcacctac aacgtcctca aggcccacgg ccacgccgtc      840
aaggtctacc gtgatcttgt tgcctccggt accattgctg ccggtgaaat tggattcaag      900
tcggatgaca actaccccat ccctgctcgc cccggcaacg ccgatgatga ggagtctgcc      960
aagcgtcacg aagcgttccg cattggtatc ttcgctcagc ctgtctacgg taacggtgac     1020
taccccgatg ttgtcaagga gactgtcggt gacatgcttc ctgctctgac cgacgaggac     1080
aagggctaca tcaagggttc cggtgacatc ttcgccatcg acggctaccg cactgacatc     1140
tcccacgctg ctctcaacgg cattgccaac tgcattcgca accagtccga ccccaactgg     1200
cccgtctgcg aagaaggctc cgaccccttc gctcacgtct accccctccgg cttcgccatt     1260 ggccagtccg ccgaccccct cagcagctgg ctggtcaact ctgctccctt catccgtgac     1320
cagctcaagt tcctgaccca gacctacccc gccaagggtg gtatctactt ctctgagttc     1380
ggctgggctg aggatgccga gtacgaccgc cagctcctct accagatcac ctgggatggt     1440
ctgcgtaccc agtacctgac cgactacctg tcccagctcc tgctggccgt ccacaaggat     1500
ggcatcaacc tccgtggtgc cctcacctgg tcgttcgtcg acaactggga atggggtctt     1560
ggcatgcagc agaagttcgg tttccagttc gtcaaccagt cggatcctga cctcacccgc     1620
accttcaagc tctccgctca cgcctacgcc cagttcggcc gcaaccattt a              1671

<210> SEQ ID NO 5
<211> LENGTH: 13
<212> TYPE: DNA
<213> ORGANISM: Artificial Sequence
<220> FEATURE:
<223> OTHER INFORMATION: sets out the modified translational initiation
     sequence of the glucoamylase glaA promoter

<400> SEQUENCE: 5
caccgtcaaa atg                                                           13

<210> SEQ ID NO 6
<211> LENGTH: 1998
<212> TYPE: DNA
<213> ORGANISM: Artificial Sequence
<220> FEATURE:
<223> OTHER INFORMATION: sets out the DNA fragments containing a.o. part
```

-continued of the glucoamylase promoter and the BHT-132 encoding gene
including an EcoRI and PacI restriction site

<400> SEQUENCE: 6
gaattcaagc tagatgctaa gcgatattgc atggcaatat gtgttgatgc atgtgcttct      60
tccttcagct tcccctcgtg cagatgaggt ttggctataa attgaagtgg ttggtcgggg     120
ttccgtgagg ggctgaagtg cttcctccct tttagacgca actgagagcc tgagcttcat     180
ccccagcatc attacaccgt caaaatgatg cttcacgctg ctctccttgt tgctcttcct     240
tgcgttgtcc ttgctcgtcc cgccggtgct gtcacctacc ccggtgccat ccccctctcc     300
ctcacctcga actacgagac tcccagccct actgccattc tctctggagcc cacccccact    360 gccactggta ctgctgagct cgatgccctc tggaacttgg ttgaggctca gtaccccgtg     420
cagactgctg ccgtcaccac cctcgtcacc gttcccgatg actacaagtt cgaggccgat     480
cctcctagct acgctcttgc tggatacgag acttctgaga ttgctggtct gaagttcccc     540
aagggcttca agttcggtgt tgctggtgcc gccatccagg ttgagggtgc tgccaaggcc     600
gagggccgtg gtccctccac ctgggactac ctctgccacc actacgcctc cacccagtgc     660
aacaactacg accctgacat caccaccaac cactactacc tctacccect cgacttcgct      720 cgtctgcagc acctgggtat caacacctac tctttctcca tctcctggac tcgcatctac     780
cctcttggtg ctggctacgt caacgaggct ggtctggctc actacgatgc cgtcatccac     840
tctgccaaga agtacggctt ggagcctgtt ggtaccgtct tccactggga tactcctctg     900
agcttgatgc tcaagtacgg tgcctggcag gacaccggtg accagattgt caaggacttc     960
gtcacctacg ccaccactgt cttcaagcgc tacggcaacg aggtcaagac ctggttcacc    1020
ttcaacgagc tcgtgtgtctt ctgctctcag aactccggtc tgccctacaa cctgacctac    1080
ccagaaggca tcaactccac ctcggcggtg ttccgctgca cctacaacgt cctcaaggcc    1140
cacggccacg ccgtcaaggt ctaccgtgat cttgttgcct ccggtaccat tgctgctggt    1200
gagatcggtt tcaagtccga cgacaactac cccatccccg ctcgccccgg caacgccgat    1260
gatgaggagt ccgccaagcg tcacgaagcg ttccgtatcg gtatcttcgc tcagcccgtg    1320
tatggcaacg gtgactaccc cgatgtcgtc aaggagactg ttggtgacat gcttcccgcc    1380
ctcaccgacg aggacaaggg ctacatcaag ggctccggtg acatcttcgc cattgacggc    1440
taccgcactg atatatctca cgctgccctc aacggcattg ccaactgcat tcgcaaccag    1500 tccgaccccca actggcccgt ctgcgaagaa ggaagcgacc ccttcgctca cgtctacccc    1560
tccggattcg ccatcggtca gtctgccgac cctctgagca gctggctggt caactctgct    1620
cccttcatcc gtgaccagct caagttcctg acccagacct accctgccaa gggtggtatc    1680
tacttctccg agttcggctg ggcggaagat gcggaatacg accgtcagct cctctaccag    1740
atcacctggg atggcctgcg cacccagtac ctgaccgact acctcagcca gctcctcctt    1800
gccgttcaca aggatggcat caacctgcgt ggagcgttga cctggtcgtt cgtcgacaac    1860
tgggaatggg gcttgggaat gcagcagaag ttcggttttcc agttcgtcaa ccagtcggac    1920
cccgatctga cccgcacctt caagctctcc gcccacgcct acgctcagtt cggccgcaac    1980
cacctgtaaa ttaattaa                                                    1998

<210> SEQ ID NO 7
<211> LENGTH: 1887
<212> TYPE: DNA
<213> ORGANISM: Artificial Sequence
<220> FEATURE:

-continued

<223> OTHER INFORMATION: sets out the DNA fragments containing a.o. part
     of the glucoamylase promoter and the BHT-134 encoding gene
     including an EcoRI and PacI restriction site

<400> SEQUENCE: 7

```
gaattcaagc tagatgctaa gcgatattgc atggcaatat gtgttgatgc atgtgcttct        60
tccttcagct tcccctcgtg cagatgaggt ttggctataa attgaagtgg ttggtcgggg       120
ttccgtgagg ggctgaagtg cttcctccct tttagacgca actgagagcc tgagcttcat       180
ccccagcatc attacaccgt caaaatgatg ctccacgctg ccttgcttgt tgctctcccc       240
tgcgttgttc tcgccggtac tgctgagctc gatgccctct ggaacctggt tgaagcgcag       300
taccccgtgc agactgctgc tgtcaccact ctcgtcaccg tccccgatga ctacaagttc       360
gaggccgacc ctcctagcta cgcccttgct ggctacgaga cttctgagat cgctggtctg       420
aagttcccca agggtttcaa gttcggtgtt gctggtgctg ctatccaggt tgagggtgct       480
gccaaggccg agggccgtgg tcccagcacc tgggactacc tctgccacca ctacgccagc       540
acccagtgca acaactacga ccccgatatc accaccaacc actactacct gtaccctctg       600
gacttcgctc gcttacaaca cctgggcatc aacacctact ctttctccat cagctggact       660
cgtatctacc cccttggtgc tggatacgtc aacgaggctg gtcttgctca ctacgatgcc       720
gtcatccact ccgccaagaa gtacggcttg gagcctgttg gtaccgtctt ccactgggat       780
actcctcttt ctctgatgct caagtacggt gcctggcagg acactggtga ccagattgtg       840
aaggacttcg tcacctacgc caccaccgtc ttcaagcgtt acggcaacga ggtcaagacc       900
tggttcacct tcaacgagcc tcgtgtcttc tgctcgcaga actccggtct gccctacaac       960
ttgacttacc ccgagggtat caactccacc tccgccgtct tccgctgcac ctacaacgtc      1020
ctcaaggccc acggccacgc cgtcaaggtc taccgtgatc ttgttgcctc cggtaccatt      1080
gctgccggtg aaattggatt caagtcggat gacaactacc ccatccctgc tcgccccggc      1140
aacgccgatg atgaggagtc tgccaagcgt cacgaagcgt tccgcattgg tatcttcgct      1200
cagcctgtct acggtaacgg tgactacccc gatgttgtca aggagactgt cggtgacatg      1260
cttcctgctc tgaccgacga ggacaagggc tacatcaagg gttccggtga catcttcgcc      1320
atcgacggct accgcactga catctcccac gctgctctca cggcattgc caactgcatt      1380 cgcaaccagt ccgaccccaa ctggcccgtc tgcgaagaag ctccgaccc cttcgctcac      1440 gtctacccct ccggcttcgc cattggccag tccgccgacc ccctcagcag ctggctggtc      1500
aactctgctc ccttcatccg tgaccagctc aagttcctga cccagaccta ccccgccaag      1560
ggtggtatct acttctctga gttcggctgg gctgaggatg ccgagtacga ccgccagctc      1620
ctctaccaga tcacctggga tggtctgcgt acccagtacc tgaccgacta cctgtcccag      1680
ctcctgctgg ccgtccacaa ggatggcatc aacctccgtg gtgccctcac ctggtcgttc      1740
gtcgacaact gggaatgggg tcttggcatg cagcagaagt tcggtttcca gttcgtcaac      1800
cagtcggatc ctgacctcac ccgcaccttc aagctctccg ctcacgccta cgcccagttc      1860
ggccgcaacc atttataaat taattaa                                          1887
```

LACTOSE REDUCED DAIRY POWDER

CROSS-REFERENCE TO RELATED APPLICATIONS

This application is the National Stage entry of International Application No. PCT/EP2021/055888, filed 9 Mar. 2021, which claims priority to European Patent Application No. 20161956.6, filed 10 Mar. 2020.

REFERENCE TO SEQUENCE LISTING SUBMITTED AS A COMPLIANT ASCII TEXT FILE (.TXT)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_2919208-591000_ST25.txt" created on 9 Feb. 2023, and 21,457 bytes in size) is submitted concurrently with the instant application, and the entire contents of the Sequence Listing are incorporated herein by reference.

BACKGROUND

Field

The invention relates to the field of dry or powder dairy compositions.

Description of Related Art

Generally, dairy powders are produced to preserve the nutrition of dairy for longer periods of time. Yet another advantage of dairy powders is that their transportation costs are severely reduced when compared to fluid dairy.

Dairy powders can be produced from milk or whey that is made lactose-free via the batch process. In this process the milk or whey is treated with a lactase enzyme before the concentration and drying of the product. A major problem is the presence of a high concentration of monosaccharides in the treated liquid dairy, leading to a drop in the glass-transition temperature. Hence, this product will lead to fouling of the spray dryer when the drying conditions are not adapted [Torres et al., 2017, technological aspects of lactose-hydrolyzed milk powder, Food Research International 101, 45-53]. The much milder spray drying conditions required, dramatically decreases productivity of the drying process, and increases costs. Additionally, the lactose-free milk (or whey) powder is highly hygroscopic, leading to caking during storage when not packaged with extra caution. Due to these challenging technical problems, lactose-free dairy powders are still a small market, in contrast to regular milk powders.

EP0458358 B1 (Snow Brand) describes a process for producing skim milk powder containing 10-15% by weight of galacto-oligosaccharides (GOS) by concentrating skim milk and incubating the concentrated milk with beta-galactosidase, followed by enzyme inactivation and spray-drying. The produced product is not lactose-free.

WO2013/182686 (DuPont) describes a polypeptide having transgalactosylating activity which is used to produce GOS-comprising yogurt. The produced product is not lactose-free. WO2013/182686 does not relate to dairy powder.

WO 2015/086746 (DuPont) describes a method for producing a milk product containing a stable amount of GOS, where the product needs to be heat-treated after production to inactivate the enzyme. The produced product is not lactose-free. Dairy powder is not described.

WO2018/210821 (Novozymes) describes a method for producing a milk product starting from a milk substrate comprising at least 20 wt % lactose and contacting the milk substrate with an enzyme having transgalactosylating activity. The produced product is not lactose-free.

WO2020/117548 (DuPont) describes a method for preparing a low lactose milk-based product having GOS fiber the method having the steps of providing a milk-based substrate comprising lactose; treating said milk-based substrate with a transgalactosylating enzyme to provide GOS fiber and remaining lactose; deactivating the transgalactosylating enzyme, contacting the milk-based substrate having GOS fiber with a lactase to degrade the remaining lactose to provide the low lactose milk-based product having GOS fiber; and deactivating the lactase.

The disadvantage of the prior art methods is that the transgalactosylating enzyme needs to be inactivated before the lactase is added and/or that the sequential use of the transgalactosylating enzyme and the lactase are time consuming and/or that the obtained product is not lactose free and/or that the milk substrate needs to comprise increased levels of lactose and/or that the prior art methods are complex and/or that spray drying of lactose free powder shows technical problems and/or that the produced GOS is broken down.

SUMMARY

The aim of the present invention is to provide a method for producing a lactose reduced (preferably lactose free) dairy powder which, for example, does not dramatically decrease the productivity of the drying equipment, i.e. the invention aims at increasing the drying capacity and/or to decrease the production time, compared with the capacity and production time of the same drying equipment which is used to dry a comparable lactose reduced dairy powder which does not (or hardly not) comprise GOS. In addition or alternatively, the aim of the present invention is to produce lactose reduced (preferably lactose free) dairy powder which has improved characteristics, i.e. is less hygroscopic and/or less sticky, compared with the hygroscopicity and stickiness of a comparable lactose reduced dairy powder which does not or hardly not comprise GOS. In addition or alternatively, the present invention aims to reduce the mass loss in lactose reduced (preferably lactose free) milk powder production. In addition or alternatively, the present invention aims to reduce the brown color formation of lactose reduced (preferably lactose free) milk powder formed during drying or storage. In addition or alternatively, the present invention aims at improving, such as simplifying, prior art methods.

The invention provides a method for producing a lactose reduced dairy powder comprising (i) treating a lactose comprising milk-based substrate with a first enzyme having transgalactosylase activity and a second enzyme having lactase activity to obtain a lactose reduced and galacto-oligosaccharides (GOS) comprising milk-based product (ii) preparing lactose reduced dairy powder from said lactose reduced and GOS comprising milk-based product, lactose free dairy powder comprising at least 4% (w/w) GOS, lactose free milk comprising at least 10% (w/w) GOS based on total carbohydrates and having a glucose/galactose ratio of >1.2, milk comprising <0.1% lactose, at least 10% GOS based on total (free/) carbohydrates and having a glucose/galactose ratio of >1.2, use of GOS for improving drying of a lactose reduced milk-based substrate, use of an enzyme having transgalactosylase activity and an enzyme having lactase activity for improving the drying of a lactose free milk-based substrate, and use of an enzyme having transgalactosylase activity and an enzyme having lactase activity for improving a characteristic of lactose free milk powder,

BRIEF DESCRIPTION OF THE SEVERAL VIEWS OF THE DRAWING(S)

FIG. 1: Diagram for production of lactose reduced/lactose free milk powder

SEQUENCE LISTING

SEQ ID NO: 1 sets out the protein sequence of the b-hexosyltransferase of *Sporobolomyces singularis* (BHT). This sequence consist of a signal sequence of 22 amino acids and a deduced mature protein sequence of 572 amino acids. The amino acid sequence of BHT of *Sporobolomyces singularis* is also set out in uniprot.org/uniref/UniRef90_Q564N5. This sequence is also referred to as BHT-132 or wildtype polypeptide without any deletion.

SEQ ID NO: 2 sets out the sequence of BHT-134 which is a deletion mutant derived from SEQ ID NO: 1 and the deletion starts at position 18 up to and including position 54.

SEQ ID NO: 3 sets out a codon-adapted DNA sequence for expression of SEQ ID NO: 1 in *Aspergillus niger.*

SEQ ID NO: 4 sets out a codon-adapted DNA sequence for expression of SEQ ID NO: 2 in *Aspergillus niger.*

SEQ ID NO: 5 sets out the modified translational initiation sequence of the glucoamylase glaA promoter.

SEQ ID NO: 6 sets out the DNA fragments containing a.o. part of the glucoamylase promoter and the BHT-132 encoding gene including an EcoRI and PacI restriction site SEQ ID NO: 7 sets out the DNA fragments containing a.o. part of the glucoamylase promoter and the BHT-134 encoding gene including an EcoRI and PacI restriction site

DETAILED DESCRIPTION

In a first embodiment, the invention provides a method for producing a lactose reduced dairy powder comprising (i) treating a lactose comprising milk-based substrate with a first enzyme having transgalactosylase activity and a second enzyme having lactase activity to obtain a lactose reduced and galacto-oligosaccharides (GOS) comprising milk-based product (ii) preparing lactose reduced dairy powder from said lactose reduced and GOS comprising milk-based product.

Preferably, the invention provides a method for producing a lactose free dairy powder comprising (i) treating a lactose comprising milk-based substrate with a first enzyme having transgalactosylase activity and a second enzyme having lactase activity to obtain a lactose free and galacto-oligosaccharides (GOS) comprising milk-based product (ii) preparing lactose free dairy powder from said lactose free and GOS comprising milk-based product.

The phrases "a lactose reduced dairy powder" and "a dairy powder having a reduced amount of lactose" are used interchangeably herein.

The phrases "a lactose free dairy powder" and "a dairy powder free of lactose" are used interchangeably herein.

The phrases "lactose comprising milk-based substrate" and "milk-based substrate comprising lactose" are used interchangeably herein.

The phrases "a lactose reduced, galacto-oligosaccharides (GOS) comprising milk-based product" and "a lactose reduced and galacto-oligosaccharides (GOS) comprising milk-based product" and "a milk based product having a reduced amount of lactose and comprising galacto-oligosaccharides (GOS)" are used interchangeably herein.

The term "dairy powder" as used herein refers to a dry powder prepared from a milk-based product. The dairy powder can be milk or whey powder. Examples of milk powder are skim milk powder, semi-skimmed milk powder, full fat milk powder, butter milk powder, milk protein concentrate (MPC) powder, and examples of whey powder are sweet whey powder or acid whey powder, whey protein concentrate (WPC) powder, and whey permeate powder.

Preferably, the dairy powder is milk powder and more preferably, the dairy powder is lactose free milk powder and hence the invention provides a method for producing a lactose free milk powder comprising (i) treating a lactose comprising milk-based substrate with a first enzyme having transgalactosylase activity and a second enzyme having lactase activity to obtain a lactose free and galacto-oligosaccharides (GOS) comprising milk-based product (ii) preparing lactose free milk powder from said lactose free and GOS comprising milk-based product.

The term "milk" as used herein refers to the lacteal secretion obtained from any mammal, such as cows, sheep, goats, camels or buffaloes. Preferably, the milk is cow's milk.

The term "milk-based substrate" as used herein refers to any raw and/or processed milk material. The milk-based substrate may have been subjected to treatments known in the art such as—for example—homogenization, pasteurization, sterilization or an extended shelf life (ESL) treatment or an ultra-heat treatment (UHT).

The milk-based substrate may be skim milk, full fat milk, semi-skimmed milk, condensed milk, reconstituted (skim) milk, butter milk, milk protein concentrate (MPC), or whey such as sweet whey or acid whey, whey protein concentrate (WPC), whey protein isolate (WPI) or whey permeate.

Preferably, the milk-based substrate may be skim milk, full fat milk, semi-skimmed milk, condensed milk, reconstituted (skim) milk, butter milk or milk protein concentrate (MPC).

The milk-based substrate comprises lactose and hence the milk-based substrate is referred to as "a lactose comprising milk-based substrate". In general, cow's milk comprises approximately 5% lactose. Preferably, the milk-based substrate only comprises the lactose which is naturally present in the milk-based substrate. Preferably, the milk-based substrate does not comprise added lactose. Preferably, the milk-based substrate comprises lactose in the range of 4 to 10 (w/v) % lactose, preferably 4 to 8 (w/v) % and even more preferably 4 to 6 (w/v) % or 4.5 to 5.5 (w/v) % lactose.

The milk-based substrate may be concentrated. The preparation of dairy powder typically comprise, as shown in FIG. 1, an evaporation step in which the substrate is concentrated. As will be explained later on, the enzymes used in a method of the invention, may be added at different points in time during the dairy powder production and could for example be added during or after evaporation in which case the milk-based substrate is concentrated. Preferably, the milk-based substrate is concentrated such that the amount of lactose is within the range of 4 to 10 (w/v) % lactose, preferably 4 to 8 (w/v) % and even more preferably 4 to 6 (w/v) % or 4.5 to 5.5 (w/v) % lactose.

The lactose comprising milk-based substrate is incubated with a first enzyme having transgalactosylase activity, i.e. an enzyme which produces GOS from lactose.

I.e. the GOS is produced in situ which means that the GOS is produced in the milk-based substrate from the lactose present in said milk-based substrate. Preferably, a method, use or product according to the invention does not comprise added GOS (i.e. non in situ produced GOS).

Beta-galactosidases are enzymes which hydrolyse terminal non-reducing beta-D-galactose residues in beta-D-galactosides, for example lactose is hydrolysed to galactose and glucose. These enzymes belong to the enzyme class EC 3.2.1.23. Besides hydrolysing, this enzyme class is also able to transfer galactose to other sugars and thereby produce galacto-oligosaccharides (GOS). The different enzymes of class EC 3.2.1.23 have various preferences for hydrolytic (beta-galactosidase) activity and transgalactosylase activity and the preference can be expressed for example by the ratio of transgalactosylating activity to hydrolysing activity.

The first enzyme as used in a method of the invention is more transgalactosylating then hydrolysing. The first enzyme has predominantly transgalactosylating activity.

The enzyme having transgalactosylase activity preferably belongs to subclass EC 3.2.1.23.

As used herein, the terms "enzyme having transgalactosylase activity", "enzyme having transgalactosylating activity", "transgalactosylating enzyme" and "transgalactosylase" are used interchangeably herein and all refer to an enzyme capable of transferring galactose from lactose to a hydroxyl group of, for example, lactose, D-galactose (gal) or D-glucose (glu) whereby galacto-oligosaccharides are produced.

The activity of the first enzyme (i.e. the enzymatic activity leading to the production of GOS) is allowed sufficient time to produce a certain level of GOS molecules. The exact time will depend on the enzyme used, the amount of enzyme used but also on the used temperature and the lactose concentration in the milk-based substrate. The skilled person is capable to identify an enzyme dosage, incubation temperature and incubation time to allow the production of GOS in the milk-based substrate.

The lactose comprising milk-based substrate is incubated with the first enzyme having transgalactosylase activity such that sufficient GOS has been formed, i.e. at least 10% GOS based on total carbohydrates.

A suitable commercial example of a first enzyme having transgalactosylase activity is Zymstar™ GOS, or Nurica™ from DuPont or Biolacta FN5 from Amano. Many other enzymes having transgalactosylase activity are described in the scientific literature and/or in patent literature. Enzymes capable of transgalactosylation have been isolated from a wide range of micro-organisms, including bacteria, fungi and yeasts (Torres et al. (2010) Comprehensive Reviews in Food Science and Food Safety, 9: 438-454). GOS yield from lactose can vary depending on the origin of the enzyme, lactose concentration, pH, enzyme dosage, time and temperature of the incubation.

Another suitable example of an enzyme having transgalactosylase activity is a *Sporobolomyces singularis* hexosyltransferase, a *Bacillus circulans* beta-galactosidase or a *Bifidobacterium bifidum* beta-galactosidase.

Additionally, beta-galactosidases which are predominantly hydrolytic can be modified to behave more like a transgalactosylating enzyme by using the methods described in WO2018/210820.

Most suitable are enzymes with transgalactosylase activity that produce GOS species that are not easily degraded by the enzyme having lactase activity, for example an enzyme having transgalactosylase activity which is a *Sporobolomyces singularis* hexosyltransferase.

The second enzyme used in a method of the invention also belongs to subclass EC 3.2.1.23 and is also a beta-galactosidase but with a preference for lactase activity or hydrolysing activity.

The activity of the second enzyme (i.e. hydrolysis of lactose to galactose and glucose) is allowed sufficient time to reduce the amount of lactose. Preferably, the activity of the second enzyme results in a lactose reduced, more preferably lactose-free, milk-based product. The exact time will depend on the exact enzyme used, the amount of enzyme used but also on the used temperature. The skilled person is capable to identify an enzyme dosage, incubation temperature and incubation time to allow the hydrolysis of lactose in the milk-based substrate in galactose and glucose.

A suitable commercial example of an enzyme having hydrolytic activity on lactose is Maxilact (DSM), Lactozyme (Novozymes), Saphera (Novozymes), Nolafit (Chr. Hansen), Ha-lactase (Chr. Hansen), Godo YNL-2 (Dupont) and some other enzymes described as lactases. Other suitable lactases have been described in the scientific literature and/or in patent publications.

Most preferably the enzyme having lactase activity has a preference for hydrolysing lactose, while the GOS species produced by the first enzyme having transgalactosylase activity remain intact.

As described above, beta-galactosidases can have transgalactosylase activity as well as lactase activity. The main activity depends for example on the lactose concentration in the milk-based substrate. Herein, an enzyme having transgalactosylase activity is an enzyme which (at the used conditions) has as its main activity, the production of GOS (but could have a minor lactase activity). An enzyme having lactase activity is an enzyme which (at the used conditions) has as its main activity, hydrolysis of lactose to glucose and galactose (but could have a minor activity which results in the production of GOS). Alternatively phrased, the first enzyme has predominantly transgalactosylase activity and the second enzyme has predominantly lactase activity. The skilled person is capable of selecting the right first and second enzymes. Suitable examples are provided above as well as in the examples.

The first and second enzyme are inactivated after incubation by any method known in the art which results in lowering of the enzyme activity. An example of a suitable inactivation method is a heat treatment, such as a pasteurization, or the heat treatment during the evaporation and concentration of the milk-based substrate, before spray drying. Preferably, the enzymes are completely inactivated (<1% of the initial activity remaining). Inactivation of the first enzyme may either be before the incubation with the second enzyme, but preferably at the same time as the second enzyme, after the incubation.

The used enzymes may be added as a liquid or as a solid (granulate) to the milk-based substrate.

The combined action of the first and second enzyme, result in a lactose reduced (preferably lactose free) and GOS comprising milk-based product which can be further processed into a lactose reduced (preferably lactose free) dairy powder.

A GOS can be a disaccharide (Degree of Polymerization (DP) 2, i.e. DP2) (except lactose which is not GOS), a trisaccharide (DP3), tetrasaccharide (DP4), pentasaccharide (DP5) or longer oligosaccharides.

An example of a disaccharide is galactosyl-galactose (gal-gal) or allolactose (galactosyl-beta 1-6-glucose). An example of a trisaccharide (DP3) is galactosyl-lactose (gal-gal-glu). An example of a tetrasaccharide (DP4) is galacto-syl-galactosyl-lactose (gal-gal-gal-glu) An example of a pentasaccharide (DP5) is galactosyl-galactosyl-galactosyl-lactose (gal-gal-gal-gal-glu). An example of an even longer oligosaccharide is (galactose)$_n$-lactose with n>3.

The term "DPx+ GOS" means the sum of GOS molecules having DPx or higher DP. For example the term "DP3+ GOS" means the sum of GOS molecules having DP3, DP4, DP5 etc.

The term GOS as used herein refers to the combination of DP2+ GOS. DP2+ GOS excludes lactose (which is by definition not GOS).

The level of GOS molecules can be determined by using different analysis techniques.

For example, one can determine the amount of lactose, glucose and galactose in the lactose comprising milk-based substrate and after incubation with the enzymes, determine the amount of lactose, glucose and galactose using an enzymatic analysis, NMR or HPAEC-PAD. Quantification of mono-, disaccharides can also be performed by using high-performance anion exchange chromatography with pulsed amperometric detection (HPAEC-PAD) analysis.

In yet another alternative method, GOS production can be established by reaction of an enzyme on lactose in which the amount of galactose generated is less than the amount of glucose generated at a given time.

The amount of GOS can then be determined by subtracting the sum of the amount of lactose, glucose and galactose (as present in the product) from the sum of the starting amount of lactose, glucose and galactose (as present in the substrate). The difference is then the amount of GOS. In a formula:

$$[GOS]_{product} = ([lac]+[glu]+[gal])_{substrate} - ([lac]+[glu]+[gla])_{product}$$

Determining the level of GOS with this formula can be performed in respect of a method of the invention, because the skilled person has the opportunity to determine the level of lactose in the milk-based substrate. Obviously, this determination/formula cannot be used if the level of lactose in the milk-based substrate cannot be determined, which is for example the case if one is provided with the lactose-reduced dairy powder (preferably lactose free milk powder) only. Another way to determine the level of GOS in a lactose-reduced dairy powder (preferably lactose free milk powder) will be provided later on.

The step of preparing lactose reduced (preferably lactose free) dairy powder from said lactose reduced (preferably lactose free), GOS comprising milk-based product, is performed using techniques which are well known in the art.

Typically, the dairy powder is made by evaporation and drying the produced lactose reduced, GOS comprising milk-based product to dryness. Drying is typically performed by spray drying, drum drying or freeze drying. Preferably the dairy powder is obtained by spray drying.

An example of a suitable scheme for producing a lactose reduced dairy powder is provided in FIG. 1. Preferably, the enzymes are added (at the same time or sequentially, preferably sequentially) when the milk is in cold storage. Such a storage is typically already present at a dairy powder plant and does not need additional equipment or changes to the dairy powder production process. Alternatively, the enzymes are added during or after evaporation.

As described above, the invention provides in a first embodiment, a method for producing a lactose reduced dairy powder comprising (i) treating a lactose comprising milk-based substrate with a first enzyme having transgalactosylase activity and a second enzyme having lactase activity to obtain a lactose reduced and galacto-oligosaccharides (GOS) comprising milk-based product (ii) preparing lactose reduced dairy powder from said lactose reduced and GOS comprising milk-based product.

Different surprising results have been noted by the inventors of the present patent application (when compared to the situation in which no, hardly no or low levels of GOS are present in lactose free milk), such as an increased glass transition temperature, an improved drying capacity of the (spray) dryer, a reduced loss of the (spray) dryer capacity and a reduction of the (spray) drying costs.

Hence, the invention alternatively provides a method for improving (increasing) the drying capacity of a (spray) dryer for lactose reduced (preferably lactose free) milk powder a method for improving (decreasing) the drying time for lactose reduced (preferably lactose free) milk powder a method for improving (increasing) the drying speed for lactose reduced (preferably lactose free) milk powder a method for improving (decreasing) the hygroscopic behaviour of lactose reduced (preferably lactose free) milk powder a method for improving (decreasing) the stickiness of lactose reduced (preferably lactose free) milk powder a method for improving (reducing) the brown color formation of lactose reduced (preferably lactose free) milk powder wherein any of said method comprises (i) treating a lactose comprising milk-based substrate with a first enzyme having transgalactosylase activity and a second enzyme having lactase activity to obtain a lactose reduced and galacto-oligosaccharides (GOS) comprising milk-based product (ii) preparing lactose reduced dairy powder from said lactose reduced and GOS comprising milk-based product.

Another different surprising result is that a milk-based product could be prepared which comprises at least 10% (w/w) GOS (based on total carbohydrates) and is lactose-free. Hence, the invention also provides a method for preparing a milk-based product which comprises at least 10% (w/w) GOS (based on total carbohydrates) and is lactose free, said method comprising treating a lactose comprising milk-based substrate with a first enzyme having transgalactosylase activity and a second enzyme having lactase activity to obtain a lactose free and galacto-oligo-saccharides (GOS) comprising milk-based product.

The already provided definitions, apply to these embodiments as well.

The (lactose reduced and GOS comprising) milk-based product as obtained by all the above described methods (as an intermediate product), comprises at least 10% GOS based on total carbohydrates. The term "total carbohydrates" in a milk-based substrate is defined as the sum of the concentrations of glucose, galactose, lactose and GOS.

As used herein, the term "lactose reduced and GOS comprising milk-based product" refers to a lactose reduction to 0.5 (w/v) % or 0.1 (w/v) %. The term "lactose free, GOS comprising milk-based product" is used to refer to a lactose reduction to <0.01% (w/v) (<0.1 g/L).

The term lactose free dairy powder (preferably lactose free milk powder) refers to a lactose reduction to <0.1% (w/w) (<1 g/kg).

Hence, the invention provides a method for producing a lactose reduced (preferably lactose free) dairy powder comprising (i) treating a lactose comprising milk-based substrate with a first enzyme having transgalactosylase activity and a second enzyme having lactase activity to obtain a lactose reduced (preferably lactose free) and galacto-oligosaccharides (GOS) comprising milk-based product (ii) preparing lactose reduced (preferably lactose free) dairy powder from said lactose reduced (preferably lactose free) and GOS comprising milk-based product, wherein the lactose in said milk-based product is reduced to 0.5 (w/v) %, preferably 0.1 (w/v) % lactose, or wherein the lactose in said milk-based product is reduced to <0.01 (w/v) % lactose and wherein the lactose reduced, GOS comprising milk-based product is a lactose free, GOS comprising milk-based product.

The invention thus provides a method for producing a lactose free dairy (preferably milk) powder comprising (i) treating a lactose comprising milk-based substrate with a first enzyme having transgalactosylase activity and a second enzyme having lactase activity to obtain a lactose free and galacto-oligosaccharides (GOS) comprising milk-based product (ii) preparing lactose free dairy (preferably milk) powder from said lactose free and GOS comprising milk-based product, wherein the lactose in said lactose free, GOS comprising milk-based product is reduced to <0.01 (w/v) % lactose.

The GOS and lactose level in the corresponding powder will be different when compared to the level of these components in the obtained lactose reduced (preferably lactose free), GOS comprising milk-based product due to the concentration effect of the drying.

The GOS level in the dairy powder is at least 4% (w/w). Preferably, the level of GOS in the dairy powder is at least 5%, 6%, 7%, 8%, 9% or at least 10% (w/w). More preferably, the level of GOS in the dairy powder is at least 15% (w/w). The level of GOS in the dairy powder is not only dependent on the specific enzymes used but also on, for example, the fat percentage in the milk-based substrate.

The level/amount of lactose in a lactose reduced dairy powder is <5%, preferably <1% (w/w). The level of lactose in a lactose free dairy (preferably milk) powder is <0.1% lactose.

Examples of a first enzyme having transgalactosylase activity have been provide above. Yet another example of an enzyme having transgalactosylase activity is a *Sporobolomyces singularis* hexosyltransferase.

It is known that several basidiomycetous yeasts have potent transgalactosylation activities, and GOS production by *Sporobolomyces singularis* (formerly called *Bullera singularis*), *Cryptococcus laurentii*, *Sterigmatomyces eleviae*, *Rhodotorula minuta*, and *Sirobasidium magnum* has been reported. A major difficulty is producing these hexosyltransferases in sufficient amounts, making the commercial production of GOS with these enzymes inhibitory expensive. An obstacle in producing these enzymes is their cellular attachment and poor secretion, necessitating cell-wall extraction and extensive purification of the enzyme with poor yield (e.g. Ishikawa et al. (2005) Journal of Bioscience and Bioengineering, 4: 331-339).

To alleviate the problems with production of these GOS-producing enzymes, the gene sequence of a β-hexosyltransferase (BHT) from *Sporobolomyces singularis* was determined (Ishikawa et al (2005)). In an attempt to over-express BHT, the gene was cloned in different *Escherichia coli* strains but all enzyme was found to be insoluble, even when it was expressed as fusion protein to enhance solubility (Dagher et al (2013) Applied and Environmental Microbiology, 79: 1241-1249). Expression of the same gene in *Pichia pastoris* in frame with an α-mating factor signal sequence (αMF) did, however, result in the secretion of a small amount of BHT. The highest secretion of 9.8 mg BHT per liter culture was found using a construct where a potential secretion signal at position 1-22 of the BHT sequence was deleted and the αMF signal sequence was used instead, and a HIS tag was attached to the C-terminal end of the BHT sequence (WO2014/089558 A1). It was concluded in WO2014/089558 that "neither αMF nor the BHT leader secretion signal could fully complete the secretion of rBHT-HIS which may be related to the presence of a transmembrane region predicted between amino acids 177-199".

The inventors of the present applications have been able to produce the beta-hexosyltransferase from *Sporobolomyces singularis* in sufficient amounts using *K. lactis* and *A. niger* as a production host. Both hosts produce sufficient quantities of a hexosyltransferase from *Sporobolomyces singularisis*. Preferably, the used hexosyltransferase from *Sporobolomyces singularisis* a truncation variant of the wildtype sequence. An example of a suitable variant is described herein within the experimental part.

Preferably, the used hexosyltransferase from *Sporobolomyces singularis* (produced in *A. niger* or *K. lactis*) has at least 80% sequence identity to SEQ ID NO: 1 or 2. For the purpose of this invention, it is defined herein that in order to determine the percentage of sequence identity of two amino acid sequences or of two nucleic acid sequences, the sequences are aligned for optimal comparison purposes. In order to optimize the alignment between the two sequences gaps may be introduced in any of the two sequences that are compared. Such alignment can be carried out over the full length of the sequences being compared. In case specific positions are described these positions should also be used in a comparison. The sequence identity is the percentage of identical matches between the two sequences over the reported aligned region.

A comparison of sequences and determination of percentage of sequence identity between two sequences can be accomplished using a mathematical algorithm. The skilled person will be aware of the fact that several different computer programs are available to align two sequences and determine the identity between two sequences (Kruskal, J.

B. (1983) An overview of sequence comparison In D. Sankoff and J. B. Kruskal, (ed.), Time warps, string edits and macromolecules: the theory and practice of sequence comparison, pp. 1-44 Addison Wesley). The percentage of sequence identity between two amino acid sequences or between two nucleotide sequences may be determined using the Needleman and Wunsch algorithm for the alignment of two sequences. (Needleman, S. B. and Wunsch, C. D. (1970) J. Mol. Biol. 48, 443-453). Both amino acid sequences and nucleotide sequences can be aligned by the algorithm. The Needleman-Wunsch algorithm has been implemented in the computer program NEEDLE. For the purpose of this invention the NEEDLE program from the EMBOSS package was used (version 2.8.0 or higher, EMBOSS: The European Molecular Biology Open Software Suite (2000) Rice, P. Longden, I. and Bleasby, A. Trends in Genetics 16, (6) pp 276-277, emboss.bioinformatics.nl). For protein sequences EBLOSUM62 is used for the substitution matrix. For nucleotide sequence, EDNAFULL is used. The optional parameters used are a gap-open penalty of 10 and a gap extension penalty of 0.5. The skilled person will appreciate that all these different parameters will yield slightly different results but that the overall percentage identity of two sequences is not significantly altered when using different algorithms.

After alignment by the program NEEDLE as described above the percentage of sequence identity between a query sequence and a sequence of the invention is calculated as follows: Number of corresponding positions in the alignment showing an identical amino acid or identical nucleotide in both sequences divided by the total length of the alignment after subtraction of the total number of gaps in the alignment. The identity defined as herein can be obtained from NEEDLE by using the NOBRIEF option and is labeled in the output of the program as "longest-identity".

Alternatively, the used hexosyltransferase from *Sporobolomyces singularis* (produced in *A. niger* or *K. lactis*) has at least 85%, 90% or 95, 96, 97, 98 or 99% sequence identity to SEQ ID NO: 1 or 2.

Examples of suitable milk-based substrates have been provided above and may be skim milk, semi-skimmed milk, full fat milk, pasteurized milk, UHT milk, milk having an extended shelf life, condensed milk, reconstituted (skim) milk prepared from powder, butter milk, milk protein concentrate (MPC), or whey such as sweet whey or acid whey, whey protein concentrate (WPC), or whey permeate.

In one of the aspects of the invention, the level of lactose has not been reduced in the milk-based substrate, for example the milk-based substrate has not been subjected to lactose reducing filtration techniques. In yet another aspect, the level of lactose in the milk-based has been reduced before incubation with the first and second enzyme.

A method of the invention may result in increased sweetness which is not appreciated by all people. Increased sweetness can be reduced by reducing part of the lactose present in a milk-based substrate by using well known techniques. I.e. a method of the invention may include a step to reducing the level of lactose in the milk-based substrate before treating said substrate with a first and second enzyme as described above.

The level of lactose in a milk-based substrate may be increased, for example by concentration, before treating the milk-based substrate with a first and second enzyme as described above. A typical production process for producing lactose reduced (preferably lactose free) dairy (preferably milk) powder comprises a concentration step. The evaporation step as shown in FIG. 1 is a concentration step and the enzymes used in a method of the invention can be added during and/or after evaporation. Preferably, the amount of lactose in a milk-based substrate is within the range of 4 to 10 (w/v) % lactose, preferably 4 to 8 (w/v) % and even more preferably 4 to 6 (w/v) % or 4.5 to 5.5 (w/v) % lactose.

The first and second enzyme which are used in any of the above described methods can be added simultaneously or sequentially. The inventors of the present invention noted that the best results are obtained by using the first and second enzyme sequentially wherein the enzyme having transgalactosylase activity is added first. Thus, first an amount of GOS is produced from lactose and the remaining lactose is hydrolysed to glucose and galactose by the second enzyme having lactase (hydrolytic) activity.

The invention thus provides a method for producing a lactose reduced (preferably lactose free) dairy powder (preferably milk powder) comprising
- (i) treating a lactose comprising milk-based substrate with a first enzyme having transgalactosylase activity and a second enzyme having lactase activity to obtain a lactose reduced (preferably lactose free) and galacto-oligosaccharides (GOS) comprising milk-based product
- (ii) preparing lactose reduced (preferably lactose free) dairy powder (preferably milk powder) from said lactose reduced (preferably lactose free) and GOS comprising milk-based product,
- wherein the milk-based substrate is first treated with the enzyme having transgalactosylase activity and subsequently with the enzyme having lactase activity, preferably said method does not comprise an enzyme inactivation step between the treatment with the enzyme having transgalactosylase activity and the treatment with the enzyme having lactase activity.

The skilled person is aware that some enzymes having lactase activity are capable of reducing GOS levels, especially when incubated for extended periods. The skilled person will take precautions to avoid (excessive) reduction of GOS by the enzyme having lactase activity.

The inventors of the present invention noted that very good results are obtained by using the first and second enzyme simultaneously. Thus, production of GOS from lactose by the first enzyme having transgalactosylase activity and lactose hydrolysis to glucose and galactose by the second enzyme having lactase (hydrolytic) activity are taking place at the same time.

The invention thus provides a method for producing a lactose reduced (preferably lactose free) dairy powder (preferably milk powder) comprising
- (i) treating a lactose comprising milk-based substrate with a first enzyme having transgalactosylase activity and a second enzyme having lactase activity to obtain a lactose reduced (preferably lactose free) and galacto-oligosaccharides (GOS) comprising milk-based product
- (ii) preparing lactose reduced (preferably lactose free) dairy powder (preferably milk powder) from said lactose reduced (preferably lactose free) and GOS comprising milk-based product,
- wherein step (i) is treating a lactose comprising milk-based substrate simultaneously with a first enzyme having transgalactosylase activity and a second enzyme having lactase activity to obtain a lactose reduced and galacto-oligosaccharides (GOS) comprising milk-based product.

Examples of dairy powder have been described above: a dairy powder are milk powder or whey powder. Examples of milk powder are skim milk powder, semi-skimmed milk powder, full fat milk powder, butter milk powder, MPC powder, and examples of whey powder are sweet whey powder or acid whey powder, WPC powder, and whey permeate powder. Preferably, the dairy powder is milk powder or whey powder. More preferably, the dairy powder is milk powder and most preferably, the dairy powder is lactose free milk powder.

The invention also provides a dairy powder, preferably a dairy powder obtainable by a method as described above.

A preferred dairy powder is a lactose free dairy powder comprising at least 4% (w/w) GOS.

The lactose free powder comprises at least 4% (w/w) GOS and <0.1 (w/w) % lactose. The invention thus provides a dairy powder (preferably milk powder) comprising at least 4% (w/w) GOS and <0.1% (w/w) lactose.

The amount of GOS in a dairy powder can be determined by subtracting the lactose, glucose and galactose concentration in a dairy powder, from the total amount of monosugars (glucose and galactose) after complete hydrolysis of the dairy powder with an acid lactase (based on AOAC official method 2001.02; described in the experimental part herein in more detail).

In yet another embodiment, the invention provides lactose free milk comprising at least 10% (w/w) GOS based on total carbohydrates and having a glucose/galactose ratio of >1.2 or the invention provides a milk comprising <0.01% lactose, at least 10% (w/w) GOS based on total carbohydrates and having a glucose/galactose ratio of >1.2.

Preferably, the (lactose-free) milk is UHT milk. Prior art lactose reduced UHT milk comprises considerable amounts of mono-sugars and the presence of these mono-sugars results in a Maillard reaction which subsequently results in browning of the UHT milk (especially when stored for longer periods). Especially galactose is reactive in the Maillard reaction, and hence lactose-free UHT milk with an increase in both GOS content and an increase in the ratio glucose/galactose will have a reduced chance in browning during storage. UHT milk comprising <0.01% lactose, at least 10% (w/w) GOS based on total carbohydrates and having a glucose/galactose ratio of >1.2 does not comprise considerable amounts of galactose and hence reduced or no Maillard/browning.

The inventors of the present invention show herein that the presence of GOS (preferably in situ produced GOS) in a lactose reduced milk based substrate has advantages when preparing a powder from the lactose reduced milk-based substrate. The advantages can be described as an advantage in the efficiency of the drying process and/or as advantages of the final product (i.e. dairy (preferably milk) powder) Examples of these advantages are (when compared to a lactose reduced or a lactose free milk based substrate which does not or hardly not comprise GOS): improving (increasing) the drying capacity of (spray) dryer, improving (increasing) the drying speed of the dryer, improving (reducing) the production time of the drying process, improving (reducing) the hygroscopic behaviour of lactose reduced (preferably lactose free) dairy powder, improving (reducing) the stickiness of lactose reduced (preferably lactose free) dairy powder and/or improving (reducing) the brown color formation of lactose reduced milk powder upon storage Hence, in yet another embodiment, the invention therefore provides Use of GOS for improving drying of a lactose reduced milk-based substrate. Preferably, the GOS is in situ produced GOS.

Use of GOS for improving drying of a lactose free milk-based substrate. Preferably, the GOS is in situ produced GOS.

Use of GOS for increasing the drying capacity for lactose reduced milk-based substrate. Preferably, the GOS is in situ produced GOS.

Use of GOS for increasing the drying capacity for lactose free milk-based substrate. Preferably, the GOS is in situ produced GOS.

Use of GOS for increasing the drying speed of lactose reduced milk-based substrate. Preferably, the GOS is in situ produced GOS.

Use of GOS for increasing the drying speed of lactose free milk-based substrate. Preferably, the GOS is in situ produced GOS.

Use of GOS for reducing the production time of a lactose reduced dairy powder from a lactose reduced milk-based substrate. Preferably, the GOS is in situ produced GOS.

Use of GOS for reducing the production time of a lactose free dairy powder from a lactose free milk-based substrate. Preferably, the GOS is in situ produced GOS.

Use of GOS for reducing the hygroscopic behaviour of a lactase reduced dairy powder. Preferably, the GOS is in situ produced GOS.

Use of GOS for reducing the hygroscopic behaviour of a lactase free dairy powder. Preferably, the GOS is in situ produced GOS.

Use of GOS for reducing the stickiness of a lactase reduced dairy powder. Preferably, the GOS is in situ produced GOS.

Use of GOS for reducing the stickiness of a lactase free dairy powder. Preferably, the GOS is in situ produced GOS.

Use of GOS for reducing brown color formation of lactose reduced milk powder. Preferably reduce brown color formation upon storage. Preferably, the GOS is in situ produced GOS.

Use of GOS for reducing brown color formation of lactose free milk powder. Preferably reduce brown color formation upon storage. Preferably, the GOS is in situ produced GOS.

Use of an enzyme having transgalactosylase activity and an enzyme having lactase activity for improving the drying of a lactose reduced milk-based substrate.

Use of an enzyme having transgalactosylase activity and an enzyme having lactase activity for improving the drying of a lactose reduced milk-based substrate.

Use of an enzyme having transgalactosylase activity and an enzyme having lactase activity for improving a characteristic of lactose free milk powder.

The features and definitions which are given above in the context of the method claims, equally apply to the use claims.

The invention also provides additional embodiments:

1. An isolated and/or recombinant polypeptide having transgalactosylase activity and having at least 95% sequence identity with SEQ ID NO: 2.

2. A polypeptide according to embodiment 1 having at least 96%, 97%, 98% or 99% sequence identity with SEQ ID NO: 2.

3. A polypeptide according to embodiment 1 or 2 which consists of SEQ ID NO: 2.

4. A method for producing a dairy product comprising adding an effective amount of a polypeptide according to any one of embodiments 1 to 3 to a milk substrate and allowing the polypeptide to exert its enzymatic activity.

5. A composition comprising a polypeptide according to any one of embodiments 1 to 3 and at least one component selected from salt, preservative, polyol or metal ions.

6. A dairy product obtainable by the method of embodiment 4.

7. A dairy product comprising a polypeptide according to any one of embodiments 1 to 3.

8. Use of a polypeptide according to any one of embodiments 1 to 3 for producing GOS, preferably in situ GOS.

The present invention is further illustrated by the following non-limiting Examples.

Materials and Methods

Enzymes Used in This Study

1. Maxilact LGi5000 (DSM Food Specialties): beta-galactosidase from *Kluyveromyces lactis*. The used Maxilact LGi5000 sample had an activity of 5000 NLU/ml.

2. Biolacta FN5 (Amano): beta-galactosidase from *Bacillus circulans*. The enzyme was glycated prior to use by performing the protocol as described in WO2018/210820. For this, Biolacta FN5 enzyme powder was dissolved at 10% (w/v) in 60% glucose, and incubated at 50° C. for 66 hr. The used Biolacta FN5 sample had an activity of 225 NLU/mg (before glycation).

3. BHT: β-hexosyltransferase, a transgalactosidase originating from *Sporobolomyces singularis*. The used BHT samples had an activity of 124 WBDG/ml. Procedures to produce an experimental sample of this enzyme have been described in the past (Dagher et al. (2013) Appl. Environm. Microbiol. 79 (4) 1241-1249). For this the gene encoding the BHT enzyme was cloned behind a strong promoter in a suitable production host, like *Kluyveromyces lactis* or *Aspergillus niger*, using standard technology. After fermentation of the selected recombinant expression strain, the secreted enzyme was isolated from the cleared fermentation broth and concentrated using ultrafiltration. More details on the production of a truncated BHT enzyme production are described below.

SMP Used in this Study

Nilac skimmed milk powder (SMP), NIZO, The Netherlands was used. Typical composition is 35% protein, 52% lactose, 1% fat, 8% ash and 4% moisture.

Production of a Truncated BHT Enzyme

Design of Truncated BHT

In order to predict where the wildtype full length protein sequence can be truncated the location of a linker domain was determined. The linker domain separates the putative N-terminal cell associated domain (CAD) from the catalytic domain in the enzyme. Truncation anywhere in this linker region likely results in functional soluble enzyme, as the functional domain don't lose its structural integrity. Cutting in the middle of a domain likely results in problems with the structural architecture of the enzyme, which can lead to protease sensitivity, misfolding, aggregation or other problems that prevent formation of a stable soluble enzyme product. To determine the linker region in SEQ ID NO:1, an online prediction server like IUPRED (iupred.enzim.hu) was used (settings: prediction type: structured regions, generate plot). Running this tool for SEQ ID NO:1, the output marks the N-terminal linker region running from position 38 until 55 in SEQ ID NO:1. To separate the CAD from the catalytic domain, a deletion is most preferably made of the CAD and ending somewhere in the linker domain.

REFERENCES

The Pairwise Energy Content Estimated from Amino Acid Composition Discriminates between Folded and Intrinsically Unstructured Proteins—Zsuzsanna Dosztányi, Veronika Csizmók, Péter Tompa and István Simon J. Mol. Biol. (2005) 347, 827-839.

IUPred: web server for the prediction of intrinsically unstructured regions of proteins based on estimated energy content—Zsuzsanna Dosztányi, Veronika Csizmók, Péter Tompa and István Simon Bioinformatics (2005) 21, 3433-3434.

Cloning of Truncated BHT

Two constructs with different truncations in BHT of *Sporobolomyces singularis* were designed.

BHT #132: Wild-type construct without any deletion (SEQ ID NO:1)

BHT #134: Deletion starts at position 18 up to position 54 (SEQ ID NO:2)

Codon-adapted DNA sequences for expression of the proteins in *Aspergillus niger* were designed containing additional restriction sites for subcloning in an *Aspergillus* expression vector. Codon adaptation was performed as described in WO2008/000632. The codon optimized DNA sequences for expression of these genes encoding the BHT #132 and BHT #134 protein of SEQ ID NO: 1 and SEQ ID NO: 2 in *A. niger* are shown in SEQ ID NO: 3 and SEQ ID NO: 4, respectively.

The translational initiation sequence of the glucoamylase glaA promoter was modified into 5'-CACCGTCAAA ATG-3' (SEQ ID NO:5) and an optimal translational termination sequence 5'-TAAA-3' was used in the generation of the expression constructs (as also detailed in WO2006/077258). The DNA fragments (SEQ ID NO: 6 and SEQ ID NO: 7), containing a.o. part of the glucoamylase promoter and the BHT #132 and BHT #134 encoding genes, was synthesized completely, purified and digested with EcoRI and PacI.

The pGBTOP-16 vector was linearized by EcoRI/PacI digestion and the linearized vector fragment was subsequently purified by gel-extraction. The DNA fragments were cloned into the pGBTOP-16 vector and the resulting vectors were named pGBTOPBHT #132 and pGBTOPBHT #134. Subsequently, *A. niger* GBA 306 was transformed with these vectors in a co-transformation protocol with pGBAAS-4, with strain and methods as described in WO 2011/009700 and references therein, and selected on acetamide containing media and colony purified according to standard procedures. Transformation and selection was performed as described in WO 98/46772. Strains containing the BHT #132 and BHT #134 genes were selected via PCR with primers amplifying the introduced BHT #132 and BHT #134 gene to verify presence of the BHT expression cassettes. Two transformants from each variant expressing the BHT #132 or BHT #134 genes were selected, and further replica-plated to obtain a single strain inoculum.

Fermentation of *A. niger* Strains in Microtiter Plate

Fresh *A. niger* spores from the strains generated above 2 were prepared and used for generating sample material by cultivation of the strain in 24 deep well plates (Axygen, Union City, USA) containing 3 ml fermentation medium 2 (15% w/v maltose, 6% w/v bacto-soytone, 1.5% w/v (NH4) 2SO4, 0.1% w/v NaH2PO4·H2O, 0.1% w/v MgSO4.7H2O, 0.1% w/v L-arginine, 8% w/v Tween-80, 2% w/v Basildon, 2% w/v MES, pH 6.2). The 24 deep well plates were covered with a Breathseal (Greiner bio-one, Frickenhausen, Germany) and a lid. After 6 days of growth at 34° C., 550 rpm and 80% humidity in a Microton incubator shaker (Infors AG, Bottmingen, Switzerland) 1.5 mL samples were taken, the mycelium was separated from the supernatant by centrifugation for 30 min at 4000 g and the supernatants were stored at −20° C. until further analyses.

Small amounts of the supernatants of the different cultures were analyzed on SDS-PAGE and stained using Coomassie Brilliant Blue. All transformants showed protein bands of the expected size. For example, both transformants harboring construct BHT #134 showed a clear secretion of a protein with apparent molecular weight of ~70 kDa. This size is slightly smaller than the size estimated for the wild-type BHT isolated from *S. singularis* biomass (Ishikawa et al, 2005), but much smaller than the 110 kDa recombinant BHT expressed in *Pichia pastoris* (Dagher et al, 2013). This suggests that expression of BHT #134 in *Aspergillus niger* results in production of an enzyme that is more similar to the native *Sporobolomyces* BHT.

Expression of BHT #134 in Shake Flask

The *A. niger* transformant strains were used for generation of sample material by cultivation of the strains in shake flask cultures. A useful method for cultivation of *A. niger* strains and separation of the mycelium from the culture broth is described in WO 98/46772. Cultivation was in CSM-MES (150 g maltose, 60 g Soytone (Difco), 15 g (NH4)2SO4, 1 g NaH2PO4·H2O, 1 g MgSO4·7H2O, 1 g L-arginine, 80 mg Tween-80, 20 mg Basildon, 20 g MES pH6.2 per liter medium). The shake flasks were incubated at 280 rpm and 30° C. Samples were taken from duplicate cultivations on day 6 of the fermentation, centrifuged for 10 min at 5000 rpm in a Hereaus labofuge RF and supernatants were stored at −20° C. until further analyses.

In order to obtain an estimate of the productivity of the BHT #134 transformants, all fermentation supernatants were analyzed using Bradford total protein analysis according to manufacturer's instructions (Sigma—B6916), and as also used in WO2014089558. Total protein concentration in the samples having no or hardly any additional protein expressed, were averaged and compared to the average of the samples of the BHT #134 transformants. Productivity is expressed as the difference between BHT #134 sample and the control. Results are depicted in Table 1.

TABLE 1

Productivity of BHT#134. Control is a similar cultivation of non-transformed *Aspergillus niger* CBS513.88. WO2014089558 indicates maximum prior art productivity of wild-type BHT in *Pichia pastoris*.

| | Cultivation method | Cultivation time (days) | Protein concentration (mg/l) | Productivity (mg/l) |
|---|---|---|---|---|
| Controls | MTP | 6 | 240 ± 48 | — |
| BHT#134 | MTP | 6 | 550 ± 15 | 310 |
| Control | Shake flask | 6 | 210 | — |
| BHT#134 | Shake flask | 6 | 620 | 410 |
| WO2014089558 | Shake flask | 6 | | 9.8 |

This productivity in MTP and shakeflask is much higher than the secretion of any basidiomycetous BHT described in the prior art. To our knowledge the best secretion of such enzymes was obtained with the *Sporobolomyces singularis* BHT in which the regular signal sequence was replaced by an αMF signal sequence (WO2014089558). Secretion of this construct in *Pichia pastoris* led to a productivity of 9.8 mg BHT/l in shake flask, more than a factor 50 lower than BHT #134 secretion.

Activity Determination Maxilact LGi5000 and Biolacta FN5

Beta-galactosidase activity in Maxilact LGi5000 and Biolacta FN5 was determined using the neutral lactase activity (NLU) assay essentially performed as described in the Food Chemical Codex (FCC 6) page 1124-1126.

Activity Determination BHT

The activity of BHT was determined using an assay which is essentially similar to the assay described (Workman and Day (1982) Appl. Environm. Microbiol. 44(6) 1289-1295). Assay conditions were slightly adapted and performed at 37° C. in sodium acetate buffer pH 4.40 at a p-nitrophenyl-p-D-glucopyranoside (PNPG) concentration of 4.7 mM. After termination of the reaction the pNP released was measured at 405 nm, and the enzyme activity was expressed as nanomole of p-nitrophenol released per second (BHTU).

Determination of the Lactose, Glucose, Galactose and GOS Content

Lactose, glucose and galactose content in milk-based samples were determined using a HPAEC-PAD method essentially as described by the AOAC ("AOAC official method 2001. 02 trans-Galactooligosaccharides (TGOS)," in Selected Food Products, AOAC International, Gaithersburg, Md, USA, 2005).

When the milk-based substrate and the milk-based product as described within this patent application are both available (as is the case in Example 3), the lactose, glucose and galactose concentration can be determined in both the milk-based substrate and in the milk-based product. The total GOS concentration in the milk-based product can be calculated by subtracting the lactose, glucose and galactose content in the milk-based product from the one in the milk-based substrate with the formula (1):

$$[GOS]_{product} = ([lac]+[glu]+[gal])_{substrate} - ([lac]+[glu]+[gla])_{product} \quad (1)$$

[lac]=concentration lactose in g/L
[glu]=concentration glucose in g/L
[gal]=concentration galactose in g/L
[GOS]=concentration galacto-oligosaccharides in g/L When the GOS content has to be determined in a sample of a milk-based product or milk-based powder without having the milk-based substrate available, the total galacto-oligosaccharide (GOS) content of the milk-based samples can be determined with a method similar to the standard AOAC method ("AOAC official method 2001. 02 trans-Galactooligosaccharides (TGOS)," in Selected Food Products, AOAC International, Gaithersburg, Md, USA, 2005). With the described HPAEC-PAD method the galactose, glucose and lactose concentration in the samples can be determined, before (initial) and after (final) hydrolysis of the samples with an acid lactase. The GOS content in the initial sample can be calculated by subtracting the initial measured amount of sugars from the final measured amount of sugars with the following formula (2):

$$[GOS]_{initial} = ([lac]+[glu]+[gal])_{final} - ([lac]+[glu]+[gla])_{initial} \quad (2)$$

[lac]=concentration lactose in g/L or g/kg
[glu]=concentration glucose in g/L or g/kg
[gal]=concentration galactose in g/L or g/kg
[GOS]=concentration galacto-oligosaccharides in g/L or g/kg Total carbohydrates in a milk-based substrate, a milk-based product or a milk powder is defined as the sum of the concentrations of glucose, galactose, lactose and GOS.

Determination of Glass Transition Temperature (Tg) by Differential Scanning Calorimetry (DSC)

Milk powder samples of 2.5 mg mass are weighed with a precision balance and encapsulated in (crimped) aluminum pans of known mass. An identical empty pan is used as a reference. Nitrogen is purged at a rate of 50 ml min−1. Heating-Cooling-Heating-Cooling-Heating cycles at 10K/min, in the range −80 until 120° C., are applied in a DSC apparatus (METLLER DSC 3+). A residence time of 0.5 minutes was selected at the maximum temperature for allowing moisture vaporization, simultaneous with DSC signal equilibration. Three heating-cooling cycles were performed. The first heating cycle was mainly used for evaporation of water while the $2^{nd}$ and $3^{rd}$ cycle were performed to measure Tg and establish reproducibility of the measurement.

Example 1: Skim-Milk Treated With BHT and Maxilact

A 10% (w/v) skim milk powder (SMP) solution was produced by dispersing 100 gram SMP in 900 ml tap water (40° C.) under agitation (250 rpm) during 30 min. After resting for 30 minutes at room temperature the dispersion was agitated during 24 h at 150 rpm 4° C. 5 ml samples of this milk was used for treatment with BHT for 24 hr at 8° C. BHT dosage was 1, 2, 5, or 10 BHTU/ml. Additionally 1 or 2.5 NLU/ml Maxilact LGi5000 was added at the same time with BHT, or 5 or 10 NLU/ml Maxilact LGi5000 was added after 18 hr (so incubation time with Maxilact was limited to 6 hr). Control samples were SMP solution where no enzymes were added (control A), incubation with only Maxilact at 5 NLU/ml (control C) and incubation with only BHT at 5 BHTU/ml for 24 h (control D). All reactions were stopped after incubation by heating for 10 minutes at 95° C.

Samples were split in 1 ml for sugar analysis and 4 ml portions were stored frozen for later analysis

TABLE 2

Skim milk samples treated with BHT and Maxilact. Dosage of the enzymes and incubation time with added BHT (incubation time 1) or added Maxilact (incubation time 2) is indicated.

| Sample | Enzyme 1 | Enzyme 1 BHTU/ml | Incubation time 1 (hours) | Enzyme 2 | Enzyme 2 NLU/ml | Incubation time 2 (hours) |
|---|---|---|---|---|---|---|
| 1 | BHT | 1 | 24 | Maxilact | 1 | 24 |
| 2 | BHT | 2 | 24 | Maxilact | 1 | 24 |
| 3 | BHT | 5 | 24 | Maxilact | 1 | 24 |
| 4 | BHT | 10 | 24 | Maxilact | 1 | 24 |
| 5 | BHT | 1 | 24 | Maxilact | 2.5 | 24 |
| 6 | BHT | 2 | 24 | Maxilact | 2.5 | 24 |
| 7 | BHT | 5 | 24 | Maxilact | 2.5 | 24 |
| 8 | BHT | 10 | 24 | Maxilact | 2.5 | 24 |
| 9 | BHT | 1 | 24 | Maxilact | 5 | 6 |
| 10 | BHT | 2 | 24 | Maxilact | 5 | 6 |
| 11 | BHT | 5 | 24 | Maxilact | 5 | 6 |
| 12 | BHT | 10 | 24 | Maxilact | 5 | 6 |
| 13 | BHT | 1 | 24 | Maxilact | 10 | 6 |
| 14 | BHT | 2 | 24 | Maxilact | 10 | 6 |
| 15 | BHT | 5 | 24 | Maxilact | 10 | 6 |
| 16 | BHT | 10 | 24 | Maxilact | 10 | 6 |
| Control A | | 0 | | | 0 | 24 |
| Control C | | 0 | | Maxilact | 5 | 24 |
| Control D | BHT | 5 | 24 | | 0 | |

Example 2: Skim Milk Treated With Glycated Biolacta and Maxilact

A 10% (w/v) skim milk powder (SMP) solution was produced by dispersing 100 gram SMP in 900 ml tap water (40° C.) under agitation (250 rpm) during 30 min. After resting for 30 minutes at room temperature the dispersion was agitated during 24 h at 150 rpm 4° C. 5 ml samples of this milk was used for treatment with glycated Biolacta FN5 for 24 hr at 8° C. Enzyme dosage of the glycated Biolacta FN5 preparation was 1, 2, 5 or 10 mg/ml skim milk. Additionally 1 and 2.5 NLU/ml Maxilact LGi5000 was added at the same time with glycated Biolacta, or 5 and 10 NLU/ml Maxilact LGi5000 was added after 18 hr (so incubation time with Maxilact was limited to 6 hr).

Control samples were SMP solution where no enzymes were added (control A1), incubation with only Maxilact at 5 NLU/ml (control C1) and incubation with only Biolacta at 10 mg/ml for 24 h (control D). All reactions were stopped after incubation for 24 h by heating for 10 minutes at 95° C. Samples were split in 1 ml for sugar analysis and 4 ml portions were stored frozen for later analysis.

TABLE 3

Skim milk samples treated with glycated Biolacta and Maxilact. Dosage of the enzymes and incubation time with added glycated Biolacta (incubation time 1) or added Maxilact (incubation time 2) is indicated.

| Sample | Enzyme 1 | Enzyme 1 mg/ml | Incubation time 1 (hours) | Enzyme2 | Enzyme 2 NLU/ml | Incubation time 2 (hours) |
|---|---|---|---|---|---|---|
| 1A | BioLacta | 1 | 24 | Maxilact | 1 | 24 |
| 2A | BioLacta | 2 | 24 | Maxilact | 1 | 24 |
| 3A | BioLacta | 5 | 24 | Maxilact | 1 | 24 |
| 4A | BioLacta | 10 | 24 | Maxilact | 1 | 24 |
| 5A | BioLacta | 1 | 24 | Maxilact | 2.5 | 24 |
| 6A | BioLacta | 2 | 24 | Maxilact | 2.5 | 24 |
| 7A | BioLacta | 5 | 24 | Maxilact | 2.5 | 24 |
| 8A | BioLacta | 10 | 24 | Maxilact | 2.5 | 24 |
| 9A | BioLacta | 1 | 18 | Maxilact | 5 | 6 |
| 10A | BioLacta | 2 | 18 | Maxilact | 5 | 6 |
| 11A | BioLacta | 5 | 18 | Maxilact | 5 | 6 |
| 12A | BioLacta | 10 | 18 | Maxilact | 5 | 6 |
| 13A | BioLacta | 1 | 18 | Maxilact | 10 | 6 |
| 14A | BioLacta | 2 | 18 | Maxilact | 10 | 6 |
| 15A | BioLacta | 5 | 18 | Maxilact | 10 | 6 |
| 16A | BioLacta | 10 | 18 | Maxilact | 10 | 6 |
| Control A1 | | 0 | | | 0 | 24 |
| Control C1 | | 0 | | Maxilact | 5 | 24 |
| Control D1 | BioLacta | 10 | 24 | | 0 | |

Example 3: Sugar Analysis

The sugar composition (glucose, galactose and lactose) of all samples generated in Examples 1 and 2 was analysed as described in the Materials and Methods section. The GOS content of each sample was calculated from the content of the measured sugars, as described in this section. The glucose content measured in the samples of Example 2 was corrected for the amount of glucose that was added in the sample via the glycated Biolacta sample. E.g., in control D1 10 mg/ml glycated Biolacta with 60% glucose is added, so 6 g/L glucose has been subtracted from the measurement.

TABLE 4

Lactose, glucose, galactose and GOS content of samples generated in Example 1

| Sample | Lactose (g/L) | Glucose (g/L) | Galactose (g/L) | Total GOS (g/L) | Ratio glu/gal |
|---|---|---|---|---|---|
| 1 | 5.5 | 22.8 | 17.8 | 9.5 | 1.28 |
| 2 | 3.6 | 23.2 | 17.8 | 11.0 | 1.30 |
| 3 | 2.1 | 23.4 | 17.5 | 12.6 | 1.34 |
| 4 | <0.1 | 22.3 | 16.2 | 17.1 | 1.38 |
| 5 | <0.1 | 25.9 | 22.2 | 7.5 | 1.17 |
| 6 | <0.1 | 25.7 | 22.0 | 7.9 | 1.17 |
| 7 | <0.1 | 25.9 | 22.3 | 7.4 | 1.16 |
| 8 | <0.1 | 24.0 | 20.6 | 11.0 | 1.17 |
| 9 | 1.9 | 24.2 | 19.3 | 10.2 | 1.25 |
| 10 | 1.4 | 23.6 | 18.2 | 12.4 | 1.30 |
| 11 | 1.1 | 21.8 | 16.0 | 16.7 | 1.36 |
| 12 | 1.1 | 19.3 | 12.5 | 22.7 | 1.54 |
| 13 | <0.1 | 26.5 | 21.7 | 7.4 | 1.22 |
| 14 | <0.1 | 24.4 | 20.0 | 11.2 | 1.22 |
| 15 | <0.1 | 23.2 | 18.4 | 14.0 | 1.26 |
| 16 | <0.1 | 21.0 | 16.2 | 18.4 | 1.30 |

TABLE 4-continued

Lactose, glucose, galactose and GOS content of samples generated in Example 1

| Sample | Lactose (g/L) | Glucose (g/L) | Galactose (g/L) | Total GOS (g/L) | Ratio glu/gal |
|---|---|---|---|---|---|
| Control A | 55.6 | <0.1 | <0.1 | <0.1 | n.a. |
| Control C | <0.1 | 27.8 | 25.3 | 2.5 | 1.10 |
| Control D | 32.4 | 5.3 | <0.1 | 17.9 | >53.00 |

TABLE 5

Lactose, glucose, galactose and GOS content
of samples generated in Example 2

| Sample | Lactose (g/L) | Glucose corrected (g/L) | Galactose (g/L) | Total GOS (g/L) | Ratio glu/gal |
|---|---|---|---|---|---|
| 1A | 4.1 | 22.0 | 17.0 | 6.3 | 1.29 |
| 2A | 4.0 | 21.6 | 16.3 | 7.5 | 1.33 |
| 3A | 4.2 | 22.5 | 16.4 | 6.3 | 1.37 |
| 4A | 3.5 | 20.4 | 15.7 | 9.8 | 1.30 |
| 5A | <0.1 | 26.1 | 22.2 | 1.1 | 1.18 |
| 6A | <0.1 | 24.8 | 21.1 | 3.5 | 1.18 |
| 7A | <0.1 | 23.9 | 20.7 | 4.8 | 1.15 |
| 8A | <0.1 | 23.2 | 21.0 | 5.2 | 1.10 |
| 9A | <0.1 | 23.1 | 17.8 | 8.5 | 1.30 |
| 10A | <0.1 | 23.6 | 17.6 | 8.2 | 1.34 |
| 11A | 1.3 | 21.6 | 15.2 | 11.3 | 1.42 |
| 12A | 2.2 | 20.4 | 14.7 | 12.1 | 1.39 |
| 13A | <0.1 | 24.3 | 19.4 | 5.7 | 1.25 |
| 14A | <0.1 | 23.5 | 18.4 | 7.5 | 1.28 |
| 15A | <0.1 | 23.0 | 17.5 | 8.9 | 1.31 |
| 16A | <0.1 | 21.5 | 16.7 | 11.2 | 1.29 |
| Control A1 | 49.4 | <0.1 | <0.1 | <0.1 | n.a. |
| Control C1 | <0.1 | 25.5 | 21.9 | 2.0 | 1.16 |
| Control D1 | 12.4 | 14.9 | 8.6 | 13.5 | 1.73 |

Full conversion of all lactose and GOS in the analytical method was checked by calculating the mass balance in each sample and comparing to the initial lactose content of the untreated skim milk, and was found to be satisfactory.

The results show that it is possible to generate skim milk samples with low lactase and an appreciable amount (>10% (w/w) of total carbohydrates) of GOS. Best results are obtained with the combination of BHT and Maxilact (samples #4-8 and #13-16), but also the combination of glycated Biolacta and Maxilact gives a satisfactory result (samples #13A-16A).

Example 4: Determination of Tg on Milk Powder Samples

Samples Control A, Control C, sample 4 and sample 16 (all described in Example 1) were freeze dried and the glass transition temperature (Tg) of the powders was determined using differential scanning calorimetry (DSC) as described in the Materials and Methods section. All DSC first heating curves yielded a broad endothermic peak very likely reflecting water vaporization. Subsequent DSC heating ramps (e.g. $2^{nd}$ respectively $3^{rd}$ heating) were conducted to a maximum temperature of 120 degrees C. and yielded reproducible discontinuities in the heat capacity which can be interpreted as glass transition phenomena; reproducibility between the $2^{nd}$ and the $3^{rd}$ heating ramp shows that on the one hand that water removal was successful, and also that eventual thermal induced degradation did not occur during the experiment. Tg was calculated from the onset temperature of the discontinuities in the heat capacity of the $2^{nd}$ and $3^{rd}$ temperature cycle, and is depicted in Table 6. The onset temperature is defined as the intersection point of the baseline before transition and the inflectional tangent.

TABLE 6

Tg of freeze dried skim milk samples treated
with BHT and Maxilact, compared to controls.

| | Tmax 120 degrees C. | |
|---|---|---|
| Sample | 2nd Heating Tg, C | 3rd Heating Tg, C |
| Control A | | 119.1 |
| Control C | 47.3 | 47.6 |
| Sample 4 | 70.5 | 70 |
| Sample 4 Duplicate | 70.7 | 70.5 |
| Sample 16 | 63.8 | 64.1 |

This measurement shows that Tg of the skim milk powder samples with increased GOS is clearly increased compared to regular lactose-free skim milk powder samples. An increase in Tg will lead to an improvement in drying properties and powder stability.

Example 5: Determination of Water Sorption on Milk Powder Samples

A larger amount of dissolved skim milk powder was treated with BHT and Maxilact exactly as is described in Example 1 for Control A, Control C and Sample 16. A sample of each treated skim milk was dried on a laboratory spray drier (LabPlant SD-05, Keison Products) with an inlet air temperature of 128.8° C., an outlet air temperature of 78.1° C., an evaporation capacity of 1508.9 g/h, a skim milk flow rate of 1718.5 g/h and a powder flow rate of 176.5 g/h. 3 milligram of the skim milk powders produced using this method were analyzed in a dynamic vapour sorption machine (DVS—TA instruments Q5000sa) at 50° C. Moisture content (gram water/gram sample) was followed for 15 hours.

TABLE 7

Water sorption at 50° C. in time. Water
sorption is depicted as gram/gram sample

| Time (hr) | 5 | 10 | 15 |
|---|---|---|---|
| sample 16 | 0.014 | 0.031 | 0.050 |
| Control A | 0.011 | 0.023 | 0.038 |
| Control C | 0.015 | 0.035 | 0.056 |

The produced skim milk powders were stored and visually inspected at regular time intervals. The regular SMP (control A) did not show any visual clumping, while the LF-SMP (control C) showed severe clumping after a storage for more than one week. The BHT/Maxilact treated LF-SMP (sample 16) showed a clearly lower tendency to clump compared to control C.

The invention claimed is:

1. A method for producing a lactose reduced dairy powder comprising (i) treating a lactose comprising milk-based substrate with a first enzyme having transgalactosylase activity and a second enzyme having lactase activity to obtain a lactose reduced and galacto-oligosaccharides (GOS) comprising milk-based product (ii) preparing lactose reduced dairy powder from said lactose reduced and GOS comprising milk-based product.

2. The method according to claim 1, wherein the milk-based product comprises at least 10% (w/w) GOS based on total carbohydrates.

3. The method according to claim 1, wherein the lactose in said milk-based product is reduced to 0.5 (w/v) % lactose.

4. The method according to claim 1, wherein the dairy powder comprises at least 4% (w/w) GOS.

5. The method according to claim 1, wherein the dairy powder comprises <5 (w/w) % lactose.

6. The method according to claim 1, wherein the enzyme having transgalactosylase activity is a *Sporobolomyces singularis* hexosyltransferase, a *Bacillus circulans* beta-galactosidase or a *Bifidobacterium bifidum* beta-galactosidase.

7. The method according to claim 1, wherein the milk-based substrate has not been subjected to lactose reducing filtration technique.

8. The method according to claim 1, wherein the milk-based substrate is first treated with the enzyme having transgalactosylase activity and subsequently with the enzyme having lactase activity.

9. The method according to claim 1, wherein the (i) is treating a lactose comprising milk-based substrate simultaneously with a first enzyme having transgalactosylase activity and a second enzyme having lactase activity to obtain a lactose reduced and galacto-oligosaccharides (GOS) comprising milk-based product.

10. The method according to claim 1, wherein said dairy powder is milk or whey powder.

11. Lactose free dairy powder comprising at least 4% (w/w) GOS.

12. The lactose free dairy powder according to claim 11 wherein the amount of lactose is <0.1 (w/w) % lactose.

13. Lactose free milk comprising at least 10% (w/w) GOS based on total carbohydrates and having a glucose/galactose ratio of >1.2.

14. Milk comprising <0.1% lactose, at least 10% GOS based on total (free/) carbohydrates and having a glucose/galactose ratio of >1.2.

15. The method according to claim 1, in which the GOS improves drying of the lactose reduced milk-based substrate.

16. The method according to claim 3, wherein the lactose in said milk-based product is reduced to 0.1 (w/v) % lactose.

17. The method according to claim 16, wherein the lactose in said milk-based product is reduced to 0.01 (w/v) % lactose.

18. The method according to claim 5, wherein the dairy powder comprises <1 (w/w) %-lactose.

19. The method according to claim 18, wherein the dairy powder comprises <0.1 (w/w) % lactose.

20. The method according to claim 6, wherein the enzyme having transgalactosylase activity is a glycated *Bacillus circulans* beta-galactosidase.

21. The method according to claim 8, wherein the method does not comprise an enzyme inactivation between treatment with the enzyme having transgalactosylase activity and treatment with the enzyme having lactase activity.

* * * * *